United States Patent [19]

Gyoten et al.

[11] Patent Number: 5,507,879
[45] Date of Patent: Apr. 16, 1996

[54] SENSOR UTILIZING THERMOELECTRIC MATERIAL AND METHOD FOR MANUFACTURE THEREOF

[75] Inventors: Hisaaki Gyoten, Neyagawa; Yasushi Nakagiri, Osaka; Yoshiaki Yamamoto, Katano, all of Japan

[73] Assignee: Matsushita Electric Industrial Co., Ltd., Japan

[21] Appl. No.: 72,940

[22] Filed: Jun. 8, 1993

[30] Foreign Application Priority Data

Jun. 9, 1992 [JP] Japan .................. 4-149298

[51] Int. Cl.$^6$ .................. H01L 35/02
[52] U.S. Cl. .................. 136/224; 136/201; 136/236.1; 136/238; 136/239; 136/240; 419/2; 419/66; 428/550
[58] Field of Search .................. 136/201, 224, 136/236.1, 238, 239, 240; 419/2, 66; 428/550

[56] References Cited

U.S. PATENT DOCUMENTS

| | | | |
|---|---|---|---|
| 3,082,277 | 3/1963 | Lane et al. | 136/5 |
| 3,906,721 | 9/1975 | Micheli et al. | 60/276 |
| 3,182,391 | 5/1965 | Charland et al. | 29/420.5 |
| 3,201,504 | 8/1965 | Stevens | 264/104 |
| 3,164,892 | 1/1965 | Lieberman et al. | 29/182.5 |
| 4,029,472 | 6/1977 | Micheli et al. | 23/254 E |
| 4,141,955 | 2/1979 | Obiaya | 422/95 |
| 4,465,895 | 8/1984 | Verner et al. | 136/225 |
| 4,500,742 | 2/1985 | Morimoto et al. | 136/206 |
| 4,588,520 | 5/1986 | Jayadev | 252/512 |
| 4,589,918 | 5/1986 | Nishida et al. | 75/244 |
| 4,652,849 | 3/1987 | Matsuura et al. | 338/34 |
| 4,717,788 | 1/1988 | Rauch, Sr. et al. | 136/237 |
| 4,764,212 | 8/1988 | Okumura | 75/228 |
| 5,057,161 | 10/1991 | Komabayashi et al. | 136/240 |

FOREIGN PATENT DOCUMENTS

| | | |
|---|---|---|
| 0455051 | 11/1991 | European Pat. Off. . |
| 0522182 | 1/1993 | European Pat. Off. . |
| 2532786 | 3/1984 | France . |
| 4017776 | 12/1990 | Germany . |
| 63-36583 | 2/1988 | Japan . |
| 3-148879 | 6/1991 | Japan . |
| 578187 | 7/1946 | United Kingdom . |
| 2222908 | 3/1990 | United Kingdom .......... 136/200 |

*Primary Examiner*—Donald P. Walsh
*Assistant Examiner*—Chrisman D. Carroll
*Attorney, Agent, or Firm*—Wenderoth, Lind & Ponack

[57] ABSTRACT

In a fine structure of a thermoelectric material, fine particles of a material exhibiting Seebeck effect are electrically linked in a loosely contacted state with one another without fusing, having spaces formed at clearances among the fine particles. A method of manufacturing the thermoelectric material comprises a step of compacting fine particles made of a material exhibiting Seebeck effect through a cold pressing. Also, disclosed is a sensor for quantitatively sensing a substance, which comprises a pellet of a powder thermoelectric material, where a temperature difference is generated between two points inside the piece of thermoelectric material. The sensor further includes thermocouples connected to a heater plate (6) and a cooling plate, and a controller which is electrically connected in the loop circuit of the thermocouples for detecting thermoelectric current corresponding to the temperature difference, thereby to control the heating of the heater plate.

12 Claims, 6 Drawing Sheets

SENSOR UTILIZING THERMOELECTRIC MATERIAL AND METHOD FOR MANUFACTURE THEREOF

BACKGROUND OF THE INVENTION

1. Field of the Invention

The present invention relates to an improvement of a thermoelectric material useful for power generation, refrigeration, and the like, and also to a sensor using the thermoelectric material. More specifically, the invention relates to a thermoelectric material using a material having a Seebeck effect and a sensor using the same thermoelectric material, and to a method of manufacturing the same.

2. Description of the Prior Art

The Seebeck effect is a phenomenon wherein, when a temperature difference arises between two different points of an electrically conductive material, an electromotive force is developed in proportion to the temperature difference. The electromotive force consists of two components, i.e., an electromotive force due to distribution of charge carrier density caused by a migration of charge carriers for keeping constant free energy of the charge carriers within the material, and another electromotive force due to an interaction between charge carriers and heat flow, namely, phonon flow from higher- to lower-temperature portions.

These charge carriers and phonons behave differently between a surface portion (up to about 100 Å in depth) and an internal portion of the material. Therefore, thermoelectric effects of the material such as thermal electromotive force (i.e., Seebeck electromotive force) are different between its surface portion and internal portion. For thin films having a thickness on the order up to 1 μm or fine particles having a diameter on the order up to 1 μm, the surface portion (interface portion) occupies larger part relative to the internal portion so that the thermoelectric effect in the surface portion can no longer be an ignorable phenomenon.

Generally, a surface of a thermoelectric material has atmospheric gasses such as oxygen, nitrogen, steam, carbon dioxide and the like adsorbed thereon, which, it is considered, would affect the thermoelectric effects on the surface portion (interface portion). Obeying Langmuir's adsorption isotherm, an adsorption amount of atmospheric gas increases with increasing the pressure of the atmospheric gas so that the higher the pressure of the atmospheric gas, the greater the change in the thermal electromotive force.

Thermoelectric materials capable of interconversion between temperature difference and electromotive force have been manufactured heretofore, as bulk materials, by melt-casting a thermoelectric material or calcining a powdery material at a high temperature, and their resulting fine structures are shown in FIGS. 7 and 8, respectively.

Referring to FIGS. 7 and 8, in the conventional material prepared by melt-casting a thermoelectric material, crystal grains are arranged densely and continuously although a small amount of cracks 13 and pores 14 may exist as shown in FIG. 7. In the conventional powder product calcined at a high temperature, the particles are partly fused and electrically linked to each other as shown by reference numeral 15 in FIG. 8. On the other hand, there can be obtained thin-film type thermoelectric materials formed through deposition on a glass substrate or organic membrane or other methods. In either case of the conventional methods, thermoelectric materials have been provided in a structure as dense as possible so that their electrical conductivity and mechanical strength as a bulk material would be enhanced for increased practicability.

Sensors using such thermoelectric materials are in most cases implemented by making use of a function of detecting temperature difference. Examples of such sensors include temperature sensors or electric thermometers incorporating alloy thermocouples such as iron/gold—chromel and alumel—chromel thermocouples. An example of the sensors can be found in an application for detecting an extinction of a pilot burner of a boiler by sensing a change in temperature difference.

Although there have already been developed semiconductor sensors using changes in electric resistance and sensors using enzyme electrode reactions as gas-pressure sensors or specified-substance oriented sensors, no sensors have been proposed yet to which any thermoelectric phenomenon has been applied.

Conventional thermoelectric materials have been used as materials for converting temperature difference into electricity due to thermal electromotive force or obtaining temperature difference by conducting an electric current through the materials. As for sensors using these materials, which have been applied only for detecting temperature difference, there is a difficulty in measuring other physical quantities such as gas pressure, concentration of a substance in a solution.

SUMMARY OF THE INVENTION

In order to solve the foregoing problems involved in the prior arts, an essential objective of the present invention is to provide an improvement of performance of thermoelectric materials and to provide a method of manufacturing a sensor using the thermoelectric material having Seebeck effect, allowing the sensor capable to detect a gas pressure and concentration of specific substances quantitatively.

In order to achieve the aforementioned objectives, a thermoelectric material according to the present invention comprises a structure such that fine particles of a material exhibiting Seebeck effect are electrically linked partially in a loose-contact state with one another. It is to be noted here that the term "loose-contact state" means a semipressure-contact state of fine particles to be electrically linked without fusing, having spaces formed at clearances between any adjacent fine particles when formed in a cold pressing or sintering process.

A method of manufacturing thermoelectric materials according to the present invention comprises a step of compacting fine particles exhibiting Seebeck effect through a cold press forming.

Further, a sensor for measuring gas pressures according to the present invention comprises: a piece of a thermoelectric material in which fine particles exhibiting Seebeck effect are electrically linked in a loose-contact state one another with spaces formed at clearances between adjacent fine particles; means for giving temperature difference between two points inside the piece of the thermoelectric material; and means for detecting thermal electromotive force generated between the two points in the material.

Still further, a sensor for detecting a specific substance according to the present invention comprises: a piece of thermoelectric material in which fine particles exhibiting Seebeck effect are electrically linked in a loose-contact state with one another, the piece of the theromoelectric material being combined with a material having a specificity of adsorption or reaction, having spaces formed at clearances between adjacent fine particles; means for giving temperature difference between two points inside the piece of the thermoelectric material; and means for detecting a thermal electromotive force generated between the two points.

In the above structure, a material having adsorption specificity or reaction specificity is preferably formed in a film-like state mainly on the surface of the particles of thermoelectric material.

According to a feature of the present invention, gas pressure and concentration of a specific substance can be detected correctly in a form of voltage using a thermoelectric material in which fine particles of a material exhibiting Seebeck effect are electrically linked in a loose-contact state with one another with spaces formed at clearances between adjacent fine particles.

According to a manufacturing method of the present invention, the thermoelectric material mentioned above can be manufactured efficiently and rationally.

According to another feature of the present invention, the arrangement of the sensor for measuring a gas pressure, particularly when lower than the air pressure, detects a change in the thermal electromotive force when the gas pressure of the atmosphere is varied, thereby to measure an atmospheric gas pressure.

Furthermore, by constituting a sensor by combining various types of materials having a specificity of adsorption or reaction along with a thermoelectric material, a concentration of a specific substance in a solution or an atmosphere can be detected.

When thermoelectric materials for use in sensors are so constructed that fine particles of thermoelectric materials are electrically linked partially in a loose-contact state one another, high sensitivities of the sensors can be enhanced.

Obeying Langmuir's adsorption isotherm, the amount of adsorbed atmospheric gas increases with increasing the pressure of the atmospheric gas. Therefore, the higher the pressure of the atmospheric gas, the greater the change in the thermoelectric force. Further, when the thermoelectric material is combined with various types of materials having a specificity of adsorption or reaction, adsorption of a specific substance onto the material will cause a change in the thermal electromotive force generated in the material.

Furthermore, the cold-pressed thermoelectric material according to the present invention is more strongly affected by the adsorbed gas since charge carriers and phonons traverse the adsorption layer.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE PREFERRED EMBODIMENTS

The following describes preferred embodiments of the present invention With reference to the accompanying drawings.

First, a method of producing a thermoelectric material will be explained below. In the first step, specified amounts of raw materials of Fe, Mn and Si each having purity of not less than 3N (>99.9%) were melted in an arc furnace and then crushed. In this case, Fe and Si are used as basic materials while Mn is used as a doping material. After repeating the cycle of melting/crushing process three times, the composition of the resultant material was analyzed and the ratio of the raw materials was adjusted to derive a composition of $Fe_{0.985}Mn_{0.015}Si_2$.

Next, in order to obtain a β-phase, the material having a composition of $Fe_{0.985}Mn_{0.015}Si_2$ was put into a vacuum sealed glass ample and annealed at 850° C. for eight hours in the glass ample. Then the annealed material was milled in a planetary ball mill for five minutes under an Ar gas atmosphere, and shifted through a mesh to obtain a powder material consisting of particles each having a size of about 5μm in diameter.

Then, the powder material was molded by cold pressing under a pressure in a range of 1000 to 3000 kgw/cm² at a room temperature so that the powder material was pelletized. A small amount of ethanol or acetone was added to the powder to enhance the rigidity of the pellets. That is, ethanol or acetone serves as a lubricant to remove cracks or the like in the pellets. Then, Seebeck coefficients for the pellets of the resultant material were measured under various pressures of atmospheric gas.

In this case although Mn was used as a doping material, other materials such as Co, Cr and Al may be used as a doping material.

Figure 1:
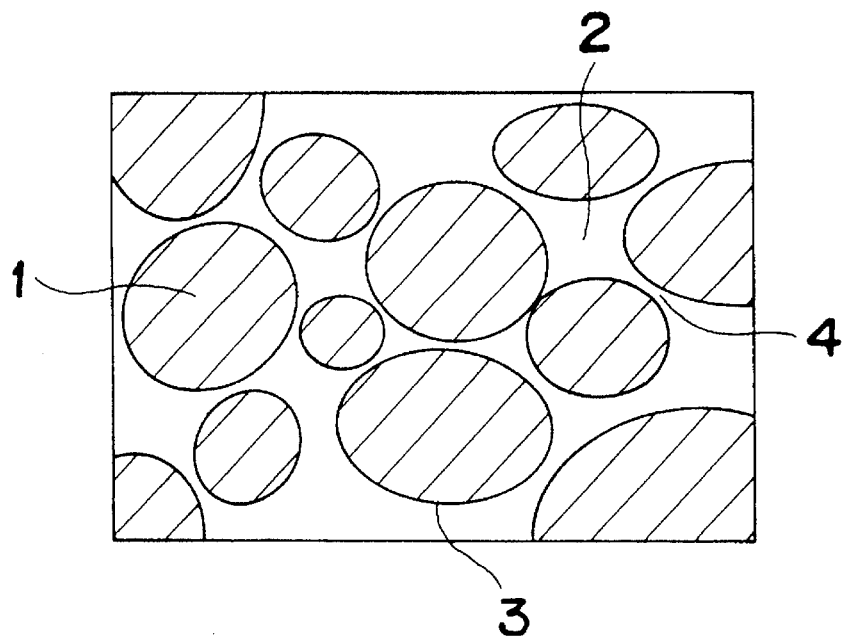
FIG. 1 is a cross sectional view of a fine structure of a thermoelectric material according to the present invention.

FIG. 1 shows a fine structure of the thermoelectric material obtained by the above mentioned processes. Each particle of the thermoelectric material having a composition of $Fe_{0.985}Mn_{0.015}Si_2$ coheres together in a loose-contact state without fusing so that atmospheric gas can be adsorbed onto a surface 3 and fed to be adsorbed to a loose-contact part 4 through a cavity 2. That is, substantially no solid or liquid material exists in the cavity 2.

Seebeck coefficients of the pellets of the thermoelectric material were measured in a container in which the conditions of atmospheric gas (i.e., pressure, species of the gas) can be adjusted.

Figure 2:
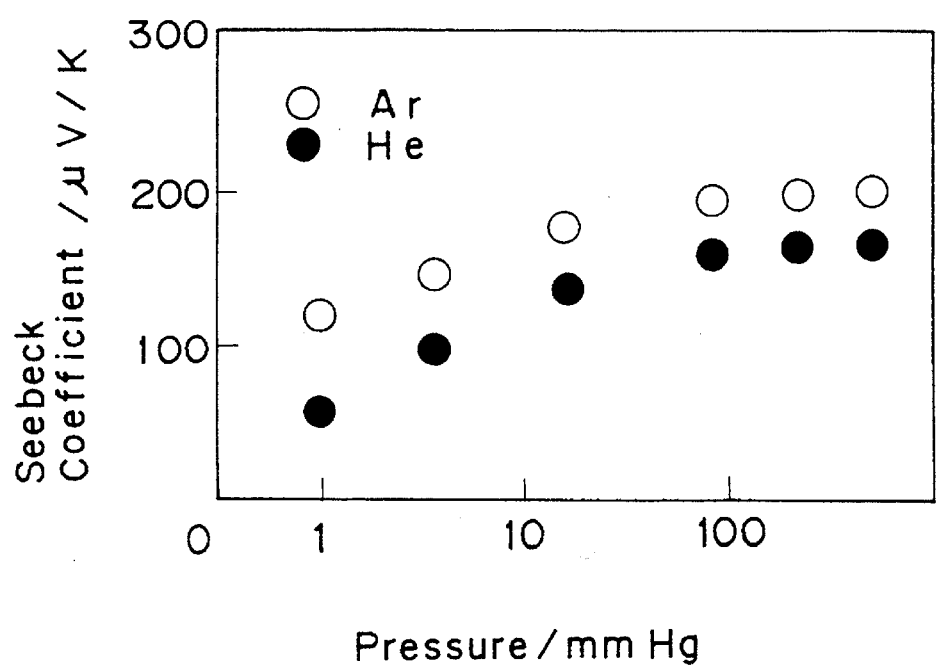
FIG. 2 is a graph representing a distribution of Seebeck coefficient of the thermoelectric material with respect to an atmospheric gas pressure according to the present invention.

FIG. 2 shows a distribution of Seebeck coefficients depending on the atmospheric gas pressure when measured under Ar and He gaseous atmospheres. Seebeck coefficient was found to largely depend upon the pressure of atmospheric gas, particularly in a range of the pressure below 100 mmHg. Also, Seebeck coefficient was found to be different between species of He and Ar gaseous atmospheres even at the same pressure. Therefore, the thermoelectric material appears to have a function of identifying species of atmospheric gas to some degree.

The influence of the pressure of atmospheric gas on Seebeck coefficient was also investigated for a basic material of $Bi_2Te_3$ except for a material of Fe-Si group. The $Bi_2Te_3$ material having purity of not less than 3N (i.e., >99.9%) was crushed and then shifted through a mesh to obtain a powder material composed of particles each having a size of about 10 μm in diameter. The powder material was pelletized under a pressure of 500 to 2000 kgw/cm². Then Seebeck coefficients for the pellets of the resultant material were measured under various pressures of atmospheric gas.

Figure 3:
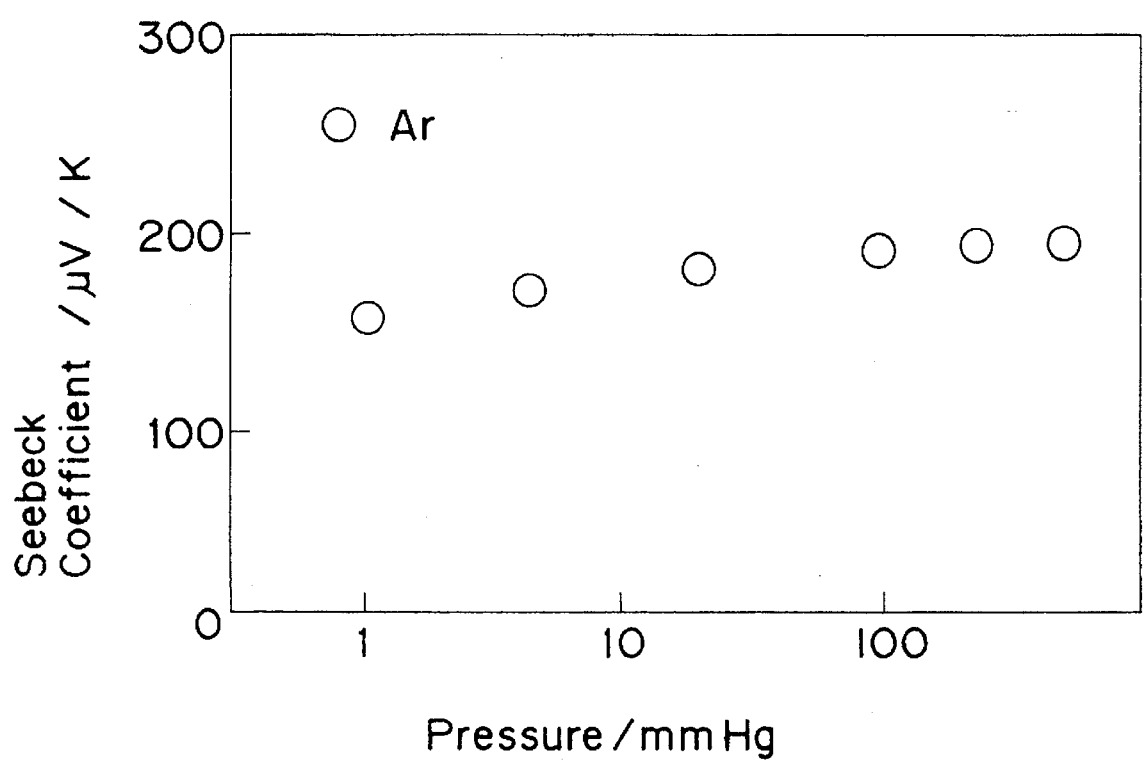
FIG. 3 is a graph representing a distribution of Seebeck coefficient of another thermoelectric material under an Ar gas atmosphere according to the present invention.

FIG. 3 shows a distribution of Seebeck coefficients depending on the atmospheric gas pressure when measured under Ar gaseous atmosphere. Seebeck coefficient was found to depend upon the pressure of atmospheric gas, particularly in a range of the pressure below 100 mmHg. It was found that Seebeck coefficients for the material of $Bi_2Te_3$ depend upon the pressure of atmospheric gas although the degree of the dependency was not so high as that of the Fe-Si group materials.

Figure 4:
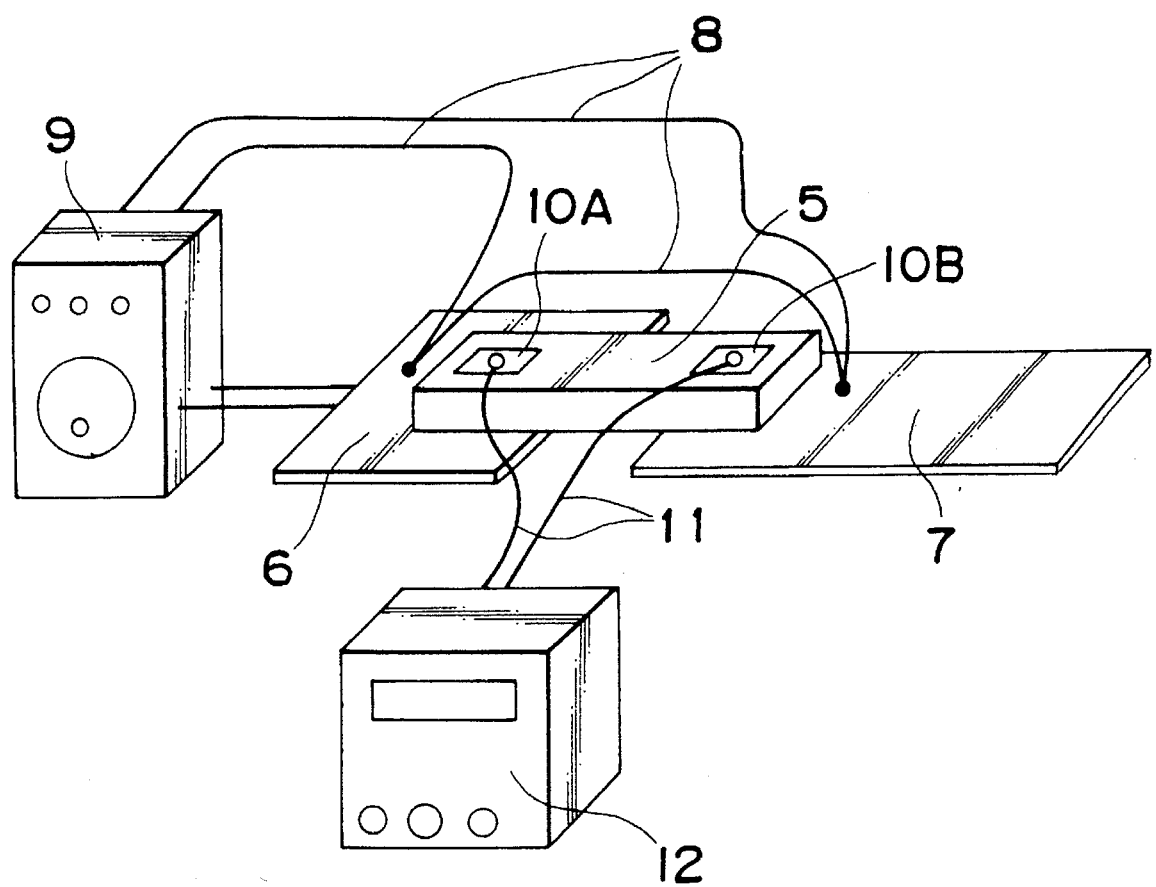
FIG. 4 is a schematic perspective view of a sensor for detecting a gas pressure or a specific substance according to the present invention.

The following describes shows an arrangement of a sensor for detecting gas pressure with reference to FIG. 4, which is assembled by using a thermoelectric material according to the present invention.

Referring to FIG. 4, a pellet 5 is provided with a rectangular shaped plate having dimensions of 2 mm×2 mm× 10 mm, which is made of the thermoelectric material having a composition of $Fe_{0.985}Mn_{0.015}Si_2$. A heater 6 is mounted to one end of the pellet 5 for heating, while a cooling plate 7 serving as a heat sink is attached to the other end of the pellet 5 for discharging heat.

Electric current is applied from a power source (not shown) to the heater 6 for heating through a controller 9. The applied electric current is controlled by the controller 9 in such a manner that the temperature difference between the both ends of the pellet 5 is kept constant at a difference value of 10° C. by providing thermocouples 8. In more detail, each of the thermocouples 8 is connected to the heater plate 6 and the cooling plate 7, where the controller 9 is electrically connected in the loop circuit of the thermocouples 8 to control the heating of the heater 6 by detecting thermoelectric current corresponding to the temperature difference.

A pair of electrodes 10A and 10B, each of which is made of silver paste, are provided in the both end portions of the pellet 5 for measuring thermal electromotive force developed in the pellet 5, where the electrode 10A is positioned in the left side in the figure corresponding to the heater plate 6 while the electrode 10B is positioned in the right side in the figure corresponding to the cooling plate 7 as shown in FIG. 4. The voltage due to the thermal electromotive force in accordance with the temperature difference is measured by means of a voltmeter 12 which is electrically connected across the both electrodes 10A and 10B via silver lead wires 11.

Ar gas was introduced into a chamber or container and it was repeatedly confirmed that the Seebeck coefficients correspond to the gas pressures in a one-by-one manner.

Figure 5:
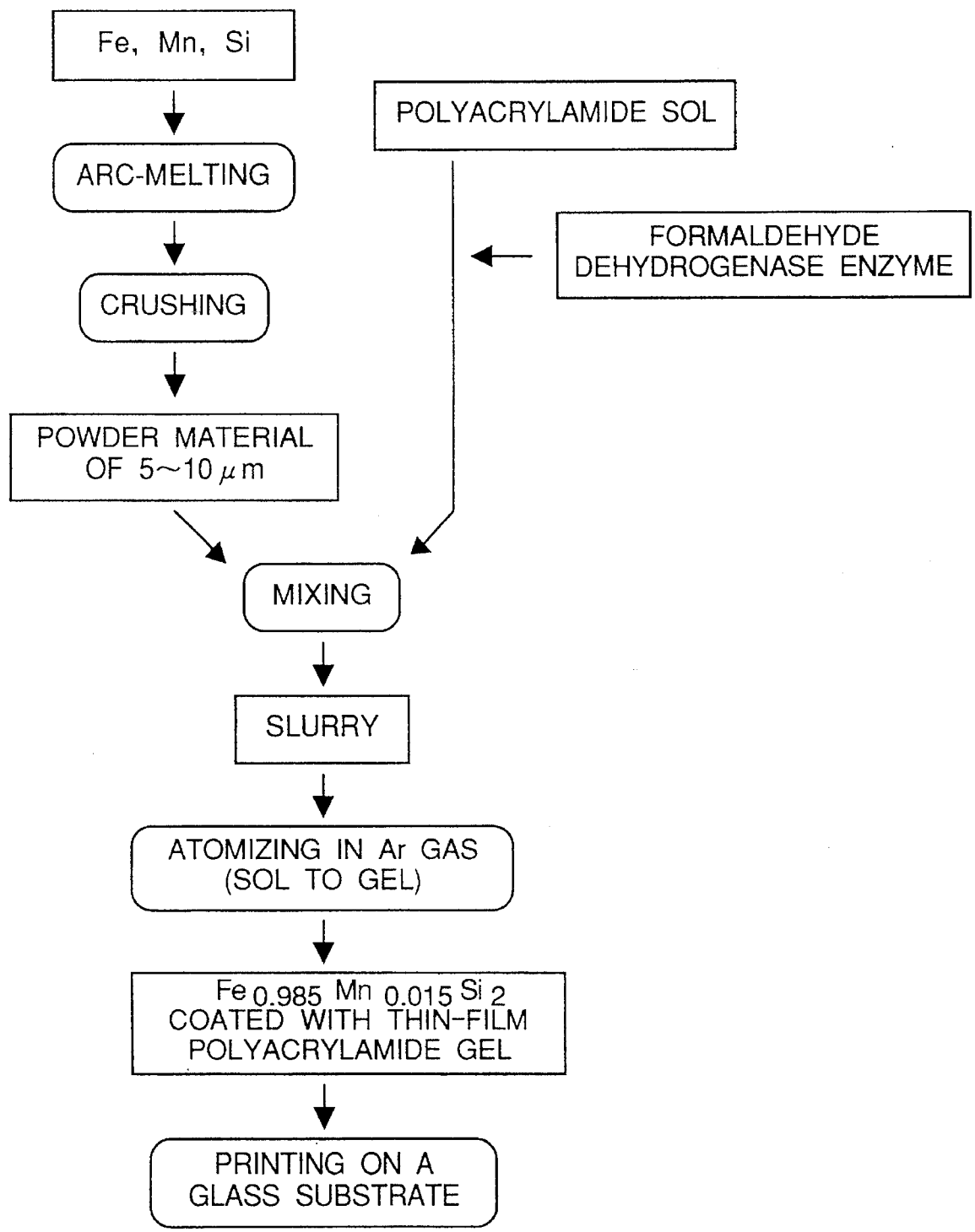
FIG. 5 is a flow chart showing a procedure of producing a sensor for quantitatively detecting a specific substance in an atmospheric gas.

Next, the following describes a method of producing a sensor for quantitatively detecting a specific substance in an atmospheric gas with reference to a flow chart shown in FIG. 5.

It is to be noted here that the basic structure of the sensor for detecting a specific substance is the same as that of the gas-pressure sensor shown in FIG. 4.

As shown in FIG. 5, a powder thermoelectric material having a composition of $Fe_{0.985}Mn_{0.015}Si_2$ was previously obtained by the production method as described before, which the material was processed into granules each having a size of 5 to 10 μm in diameter. Then, in order to obtain a material having a specificity of adsorption or reaction, formaldehyde dehydrogenase enzyme was mixed into polyacrylamide sol and further mixed with the above processed powder thermoelectric material of $Fe_{0.985}Mn_{0.015}Si_2$, thereby to obtain a slurry state, where the polyacrylamide sol is used as a supporting member. The mixed slurry material was atomized in a dried Ar gas atmosphere so that the polyacrylamide sol was gelatinized and then excessive solvent was dispersed by evaporation.

Figure 6:
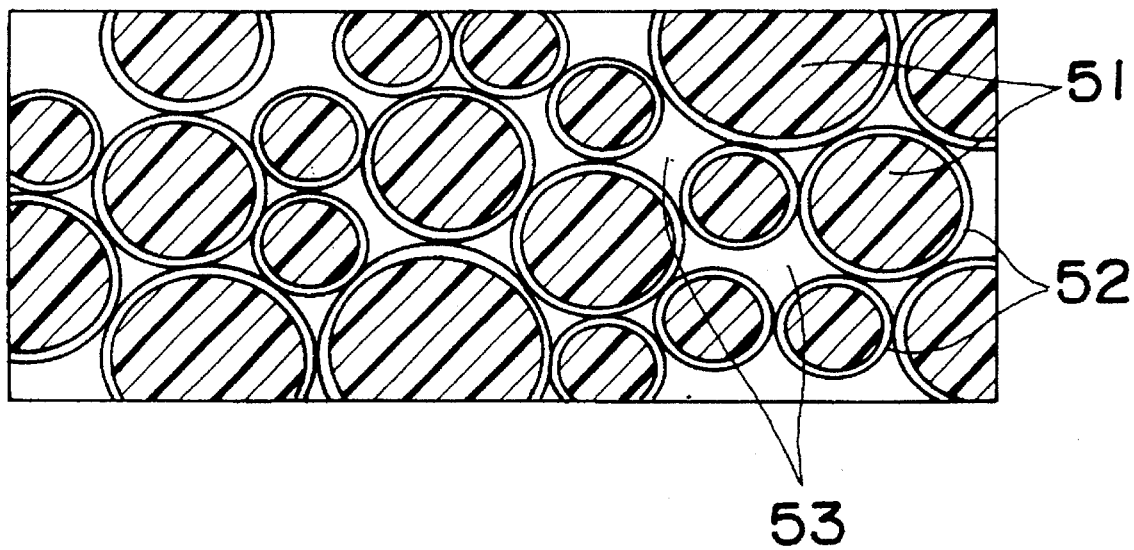
FIG. 6 is a cross sectional view of a fine structure of a thermoelectric material having Fe-Mn-Si particles coated with a thin-film like polyacrylamide gel including enzyme.
Figure 7:
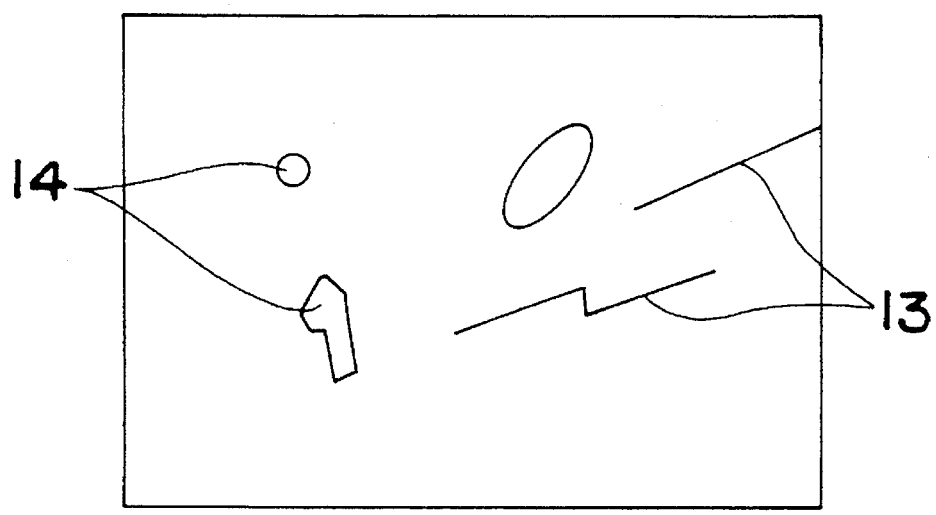
FIG. 7 is a cross sectional view of a fine structure of a conventional melt-casted thermoelectric material.
Figure 8:
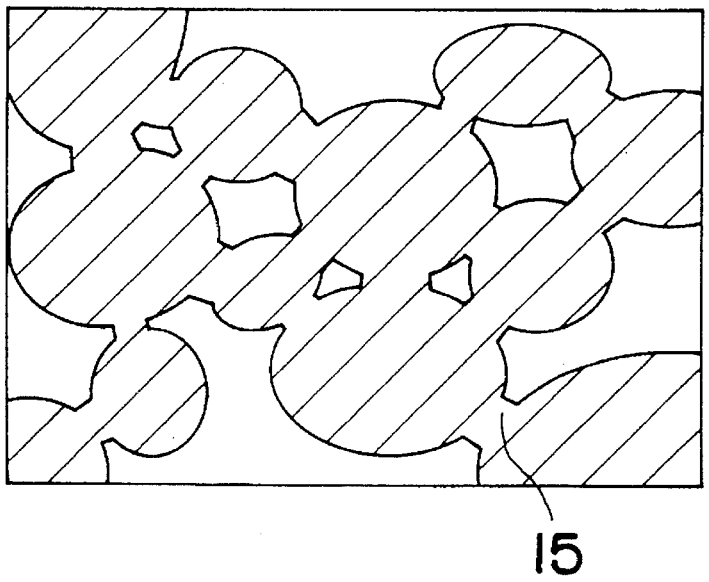
FIG. 8 is a cross sectional view of a fine structure of a conventional powder-calcined thermoelectric material.

In the resultant powder material obtained by the process mentioned above, there was contained a thin-film like polyacrylamide gel including enzyme, which was formed on the surface of the $Fe_{0.985}Mn_{0.015}Si_2$ particles, and the film thickness was 0.5–5.0 μm as shown in FIG. 6.

Referring to FIG. 6, the particles 51 of the powder material of $Fe_{0.985}Mn_{0.015}Si_2$ were coated with a thin-film like polyacrylamide gel 52 including enzyme. In this fine structure of the powder material, there were formed spaces 53, i.e., cavities among the particles. Then the obtained powder material was dispersed in an organic solvent and formed on a glass substrate through a printing method. In the same manner as that for the gas-pressure sensor, a temperature difference of 10° C. was kept constant and the variation in thermal electromotive force was traced. The measurement values of electromotive force for atmospheres of Ar gas containing formaldehyde of 1 ppm, 10 ppm and 100 ppm were respectively 2350 μV, 2550 μV and 2700 μV, which were increased by 300 μV, 500 μV and 650 μV respectively comparing to the value (2050 μV) for pure Ar gas.

The foregoing example is an application of enzyme reaction for sensing a concentration of a specific substance in a gas atmosphere. By using other enzyme systems or antigen-antibody reactions as reactions having specificities, concentration of a specific substance in a solution can also be detected and a wide variety of detectable substances can be selected.

As a method for supporting these materials having adsorption specificities, there can be used a cellulose membrane. Another method can be also adopted by fixing antibodies or enzymes directly on the surface of fine thermoelectric particles through a chemical reaction. On the other hand, although the sensitivity was not very high, gas pressures and concentrations of specific substances could be detected by using a thin film of approximately 1 μm thick instead of fine thermoelectric particles.

As described hereinabove, according to the sensing material in the embodiment, the material has a fine structure in cross section in which fine particles 1 cohere together in a loose-contact state without fusing and an adsorption of atmospheric gas or that of specific substance through an enzyme reaction occurs on the surface 3 and the loose-contact part 4 through the cavity 2 as shown in FIG. 1. When a substance is adsorbed on the surface (the interface), the thermal electromotive force changes depending upon the amount of adsorption and then the system acts as a sensor. Accordingly, a gas pressure and a concentration of a specific substance can be detected in a form of a voltage by using thermoelectric materials.

As described above, according to the present invention, gas pressures and concentrations of specific substances can be detected correctly in a form of voltage by using a thermoelectric material of the present invention by virtue of the structure that fine particles of a material exhibiting the Seebeck effect are electrically linked in a loose-contact state while spaces are formed at clearances among the particles. The sensor of the present invention is very profitable in the industry since gas pressures or concentrations of specific substances can be detected as voltage values.

Although the present invention has been fully described by way of example with reference to the accompanying drawings, it is to be noted here that various changes and modifications will be apparent to those skilled in the art. Therefore, unless otherwise such changes and modifications depart from the scope of the present invention as defined by the appended claims, they should be construed as included therein.

What is claimed is:

1. A sensor for measuring gas pressure comprising:
    a pellet of powder thermoelectric material having a fine structure in which fine particles of one compound exhibiting a Seebeck effect are made by a cold pressing are electrically linked in a state of loose contact with one another without fusing so as to exhibit said effect, having spaces formed at clearances between the fine particles;
    means for generating a temperature difference between two points inside said pellet of the thermoelectric material; and
    means for sensing a thermal electromotive force generated between the two points inside said pellet as a function of pressure.

2. The sensor is claimed in claim 1, wherein said thermoelectric material has a composition of $Fe_{0.985}Mn_{0.015}Si_2$, which is shaped in a rectangular plate.

3. The sensor as claimed in claim 2, wherein said temperature differences generating means includes a heater plate attached to one end of said thermoelectric plate for heating and a cooling plate attached to the other end of said thermoelectric plate for discharging heat.

4. The sensor as claimed in claim 2, wherein said temperature difference generating means further includes control means for controlling the temperature difference between the two points to be kept constant.

5. The sensor as claimed in claim 2, wherein said temperature difference generating means further includes thermocouples connected to the heater plate and the cooling plate, and wherein said control means is electrically connected in the loop circuit of said thermocouples for detecting thermoelectric current corresponding to the temperature difference, thereby to control the heating of the heater plate.

6. The sensor as claimed in claim 2, wherein said thermal electromotive force sensing means further includes first and second electrodes made of silver paste, which are respectively provided in the end portions of said thermoelectric plate, said first electrode being located in a position corresponding to the heater plate while said second electrode being located in position corresponding to the cooling plate.

7. The sensor as claimed in claim 6, wherein said thermal electromotive force sensing means further includes a voltmeter which is electrically connected across said first and second electrodes via silver lead wires for measuring a voltage due to the thermal electromotive force in accordance with the temperature difference.

8. A sensor for measuring gas pressure and density of a specific substance comprising:
    a pellet of powder thermoelectric material having a fine structure in which fine particles of one compound exhibiting a Seebeck effect are made by a cold pressing and are electrically linked in a state of loose contact with one another without fusing so as to exhibit said effect, having spaces formed at clearances between the fine particles;
    means for generating a temperature difference between two points inside said pellet of the thermoelectric material; and
    means for sensing a thermal electromotive force generated between the two points inside said pellet;
    and wherein said fine particles of the thermoelectric material are coated with a material having a specificity of adsorption of the specific substance.

9. The sensor as claimed in claim 8, wherein said material having a specificity of adsorption is a formaldehyde dehydrogenase enzyme mixed into polyacrylamide sol.

10. The sensor as claimed in claim 8, wherein said material having a specificity of absorption is formed in a film-like state mainly on the surface of the particles of thermoelectric material.

11. A method of manufacturing a sensor for quantitatively detecting a specific substance in an atmospheric gas comprising the steps of:
    a. producing a powder thermoelectric material having a composition of $Fe_{0.985}Mn_{0.015}Si_2$ by a method comprising:
        i. compacting fine particles made of one compound exhibiting a Seebeck effect, said compacting consisting essentially of a cold pressing to produce a thermoelectric material composed of fine particles loosely contacting each other so as to exhibit said effect, with spaces formed at clearances between the particles, and before said cold pressing, the steps of melting specified amounts of raw materials of Fe, Mn and Si, each having a purity of not less than 99.9% in an arc furnace and then crushing;
        ii. repeating the cycle of melting/crushing;
        iii. analyzing the composition of the resultant material; and
        iv. then adjusting the ratio of the raw materials to derive a composition of $Fe_{0.985}Mn_{0.015}Si_2$; and
    b. processing the resultant powder thermoelectric material into granules each having a size of 5 to 10 μm in diameter;
    c. mixing formaldehyde dehydrogenase enzyme serving as a material having a specificity of adsorption into polyacrylamide sol and mixing the resultant mixture with the powder thermoelectric material of $Fe_{0.985}Mn_{0.015}Si_2$, thereby to obtain a slurry;
    d. atomizing the mixed slurry in a dried Ar gas atmosphere thereby to gelatinize the polyacrylamide sol, dispersing excessive solvent by evaporation; and
    e. dispersing the obtained powder material in an organic solvent to be formed on a glass substrate through printing.

12. The method of manufacturing a sensor as claimed in claim 11, wherein, in the step of gelatinizing the polyacrylamide sol, a thin-film like polyacrylamide gel including enzyme is formed on the surface of the $Fe_{0.985}Mn_{0.015}Si_2$ particles, having the film thickness adjusted to 0.5–5.0 μm.

* * * * *